US005780855A

United States Patent [19]
Pare et al.

[11] Patent Number: 5,780,855
[45] Date of Patent: Jul. 14, 1998

[54] GAMMA CAMERA WITH AN IMPROVED PATIENT CARRIER BED

[75] Inventors: Christian Pierre Pare, Plaisir; Quang Trung Nguyen, Paris; Gérard Mercier, Limours, all of France

[73] Assignee: SMV International, Buc Cedex, France

[21] Appl. No.: 706,458

[22] Filed: Sep. 4, 1996

[30] Foreign Application Priority Data

Sep. 8, 1995 [FR] France .................................. 95 10795

[51] Int. Cl.⁶ ............................ A61B 6/04; G01T 1/166
[52] U.S. Cl. ........................... 250/363.02; 250/363.04; 378/209
[58] Field of Search ................... 250/363.05, 363.04, 250/363.02; 378/209

[56] References Cited

U.S. PATENT DOCUMENTS 3,763,375  10/1973  Scheninger .

FOREIGN PATENT DOCUMENTS

| 0 405 001 A1 | 1/1991 | European Pat. Off. ........... 378/209 |
| 0 517 600 A1 | 12/1992 | European Pat. Off. . |
| 2 644 688 | 9/1990 | France . |
| 3 828 087 A1 | 2/1990 | Germany ....................... 378/209 |
| 2 068 700 | 8/1981 | United Kingdom . |
| WO 88/03779 | 6/1988 | WIPO . |

OTHER PUBLICATIONS

*French Preliminary Search Report* relating to FR 95/10795.

*Primary Examiner*—Constantine Hannaher
*Attorney, Agent, or Firm*—Wolf, Greenfield & Sacks, P.C.

[57] ABSTRACT

A gamma camera equipped with at least two radiation detectors inclined in relation to each other and a patient-carrier bed including a platform which includes a window that is more transparent to radiation than the rest of the platform. The platform includes two parts defining the window therebetween and connected to each other by a lateral arch.

16 Claims, 6 Drawing Sheets

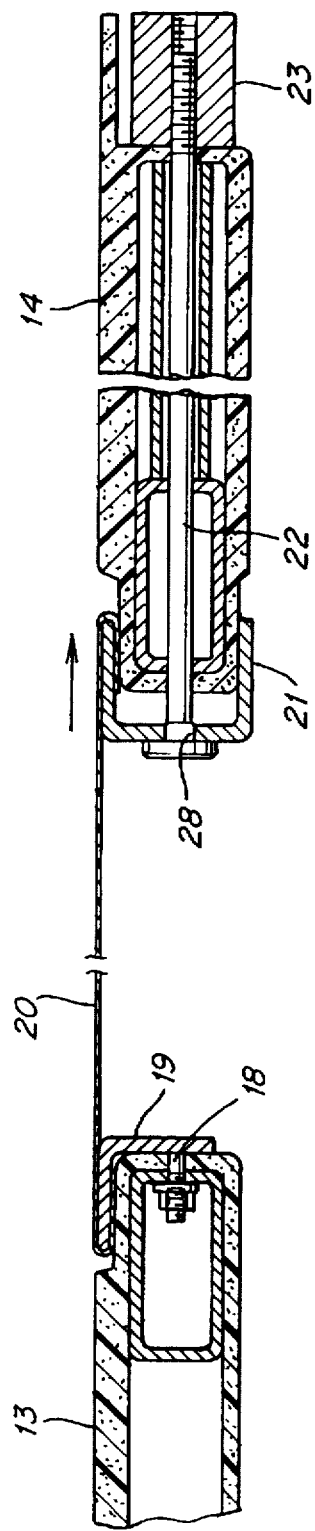
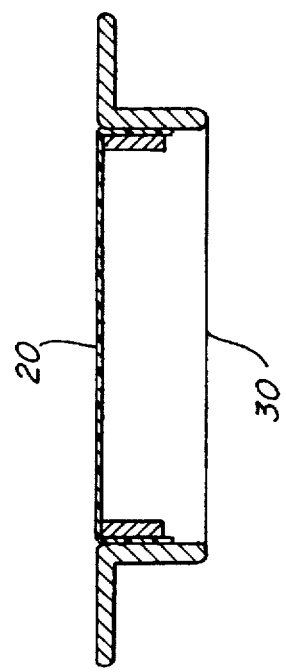
FIG. 4a
FIG. 4b

GAMMA CAMERA WITH AN IMPROVED PATIENT CARRIER BED

Gamma camera with an improved patient-carrier bed. The subject of the present invention is a gamma camera with an improved patient-carrier bed. This invention can be used for nuclear medicine especially for cardiography and mammography examinations.

Gamma cameras are radiography devices on which gamma radiations emitted by a patient or possibly X-rays emitted by a source and passing through the patient are measured. There are many types of devices very different from each other. We know of the existence of gamma cameras by patent U.S. Pat. No. 3,011,057. Gamma cameras can be of the multi-detector type. An example of two detectors can be found in patent EP-B-0 517 600.

Conventional patient-carrier beds made of wood or composite materials (for example carbon fibre) and metal frames, used in known devices, are not completely transparent to gamma- or X-radiation. The disturbances generated by the bed platform during measurements may hinder certain examinations such as cardiac tomographies. Also, certain examinations such as mammographies require that the breasts of the patient be compressed as least as possible requiring the patient to lie on her back when it would be preferable to let the breasts hang.

The aim of the invention is to overcome the above mentioned disadvantages with a solution in which a same patient-carrier bed platform will be used for the specific above mentioned examinations.

With these objectives in mind, the subject of the invention is a gamma camera equipped with at least two radiation detectors inclined in relation to each other and a patient-carrier bed including a platform which includes a window more transparent to radiation than the rest of the platform. So that the window offers an examination field as large as possible, the platform of the bed includes two parts, connected by a lateral arch and defining between them the window.

The device according to the invention is a gamma camera of known type, possessing several detectors, with a patient-carrier bed the platform of which has been subjected to certain modifications. The idea on which the invention is based was to remove a part of the hindering material from the patient-carrier bed platform to obtain a clearer image during a cardiac tomography where at least two images are taken simultaneously. Moreover, it is also very interesting to be able to let the breasts of the patient hang during a mammography. The bed could also be used for other types of examinations.

In order not to hinder the patient or the movements of the gamma camera detectors, the arch is preferably curved, as will be explained later. Indeed, using two detectors simultaneously means that the position of each of the detectors must be simultaneously taken into account. No benefits are gained in having two detectors if one of them cannot be used or if it hinders the movements of the other detector. We will use an arch with a change in curvature in relation to a curvature of the platform at a certain distance from the lateral edge of the platform.

Patients may have certain particularities, especially organs symmetrically inversed when compared with the majority of the population. An improvement consisting in making the arch removable so that it can be placed indifferently on either side of the platform makes the use of the patient carrier bed symmetrical.

Examinations using gamma cameras are fairly long, some of them around thirty minutes, and the patients must remain completely still in order not to disturb the examination. Lack of support in the patient-carrier bed platform window area may therefore be a hindrance to the patient. The patient, not being at ease, may move therefore during the examination.

Preferably, to reduce hindrance to the patient as far as possible, a sheet of material very transparent to radiation is added to the bed window. Other improvements concern the attachment method of the above mentioned sheet.

For mammographies, it may be interesting to have a separate image of the two breasts of the patient. To this end, the bed can be equipped with a removable image separator.

To stiffen the patient-carrier bed when installing the patient, to avoid distortions to the platform, it can be equipped with a removable reinforcement.

The platform of the patient-carrier bed, according to the invention, does not however permit all types of examinations which are possible with a gamma camera. Rather than using two different beds, a removable bed platform system allows the platform to be easily changed keeping the same base and therefore allows costs and the size of the equipment to be limited.

Other characteristics and advantages of the invention will come to light during the description of a gamma camera in compliance with the invention which will be given as an example. Refer to the appended drawings on which:

FIG. 4a represents an attachment method in the window for a sheet by a tensioning system shown by a longitudinal section.

FIG. 4b represents another attachment method for a sheet using a removable frame.

Figure 1:
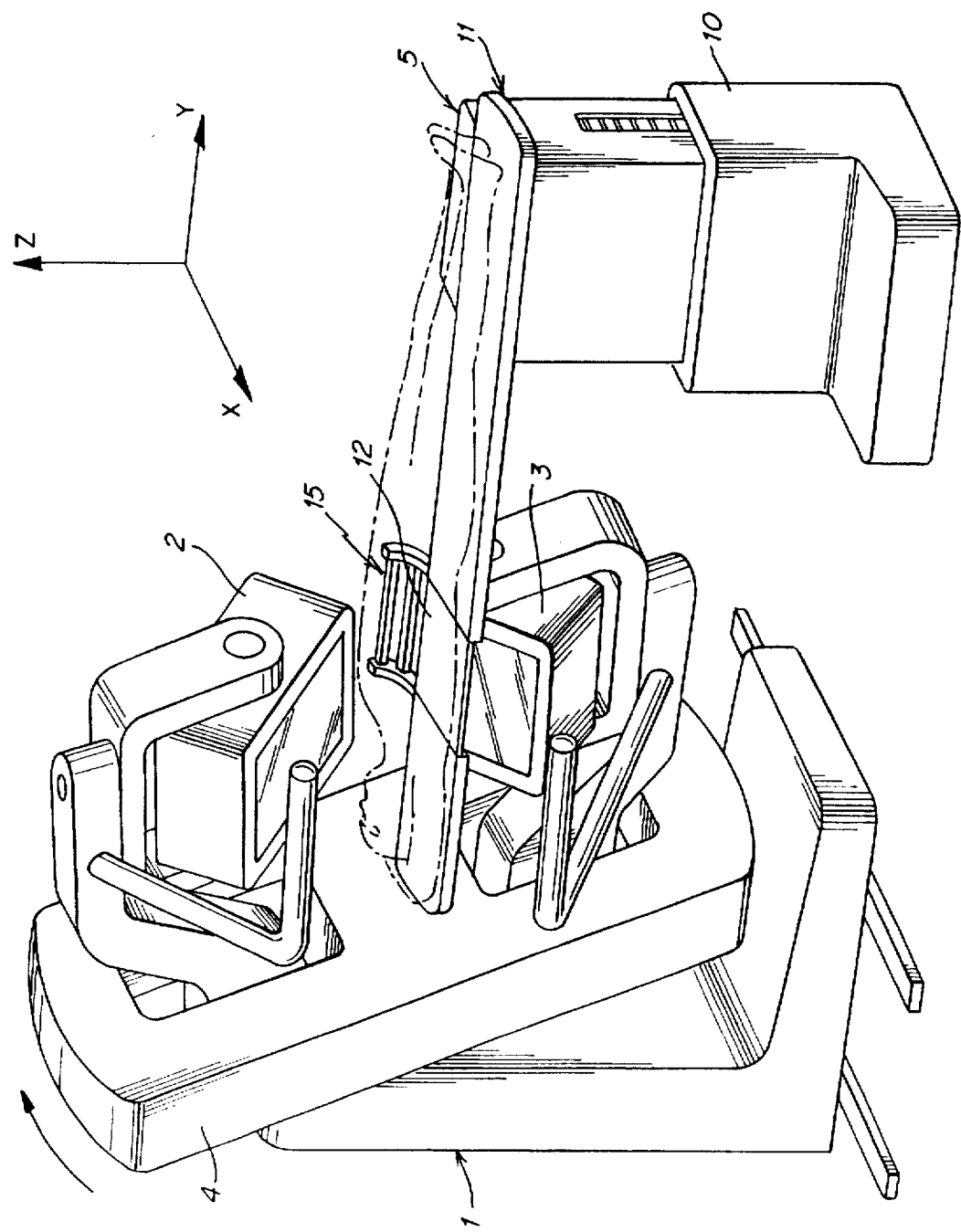
FIG. 1 represents a complete examination system with a multi-detector gamma camera, according to the invention, with a phantom view of the patient.
Figure 2:
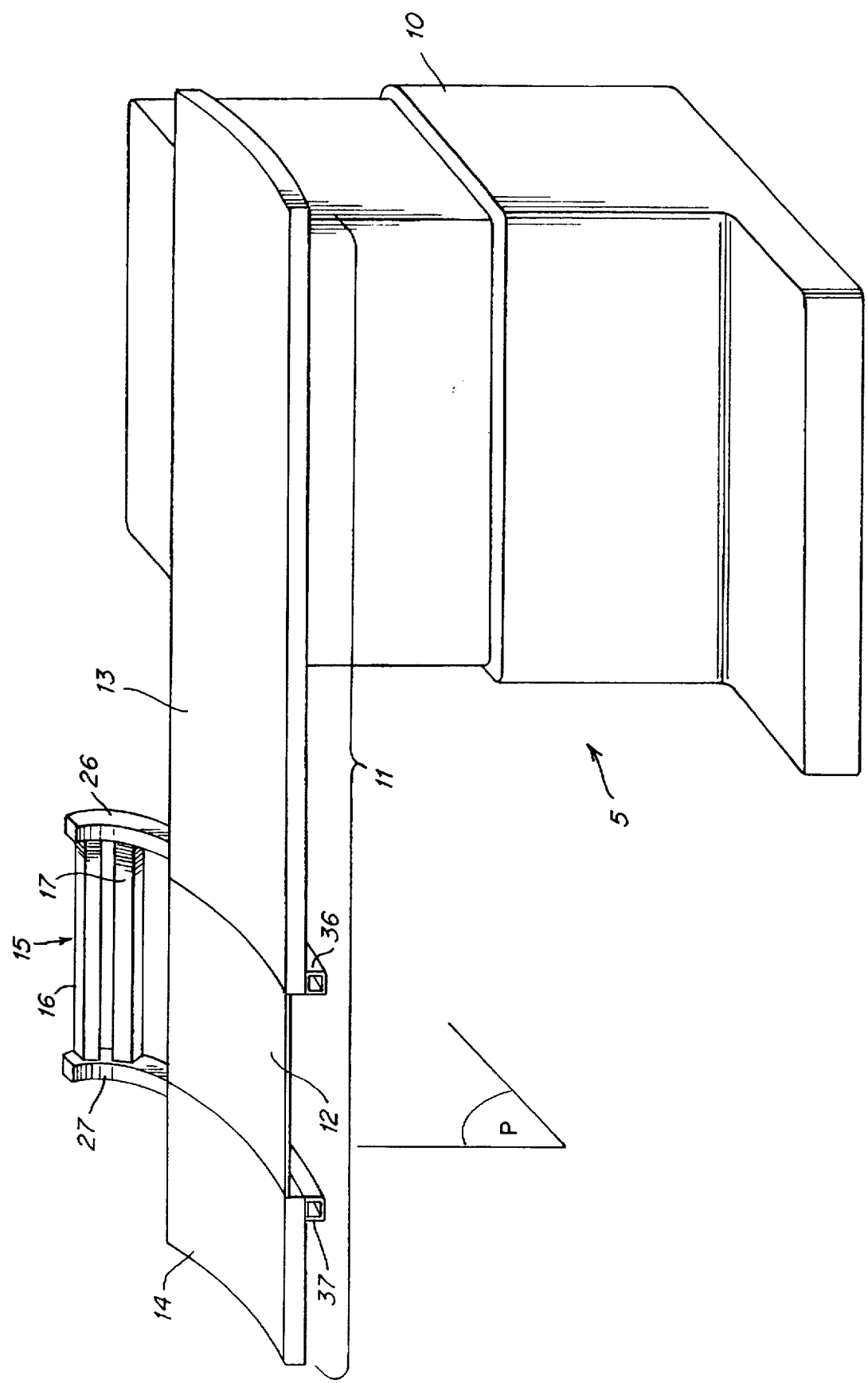
FIG. 2 represents the patient-carrier bed alone showing the arch and window.

FIG. 1 represents a gamma camera 1 including two detectors 2 and 3 which operate with a certain inclination in relation to each other. Detectors 2 and 3 are carried by a stand 4 which turns around a patient-carrier bed 5. This patient-carrier bed 5, that can be seen in more detail on FIG. 2, includes a base 10 and a platform 11.

Base 10 is telescopic and is equipped with means for movement. This provides platform 11 with complete freedom of movement in translation on the three axes X, Y and Z in space. Base 10 is also equipped with slaved motors controlled by the gamma camera 1. During the examination, the position of the platform is completely stable and controlled by gamma camera 1.

Platform 11 includes a window 12 between a first part 13 and a second part 14. An arch 15 connects first part 13 to second part 14. Second part 14 is designed to accommodate the upper part of the patient's trunk, shoulders and head, it can even include a rest for the arms when the patient is lying on his/her stomach. First part 13 supports the pelvis and the legs of the patient when stretched out.

Platform 11 must be sufficiently stiff to support the weight of any person undergoing examinations, its dimensions are, for example, a total length of 2 m, a width of 0.4 m and a thickness of 0.04 m. For this purpose, the two parts 13 and 14 include high-strength metal frames 6 and 7, for example, rectangular section extrusions measuring 20 mm×50 mm placed longitudinally along the sides of the platform are suitable. These frames are embedded in a composite material shell, for example carbon fibre. First part 13 is 1.35 m long. Second part 14 is 0.3 m long.

Connecting arch 15 extends beyond the lateral edge of patient-carrier bed 5; this means, on the one hand, that there will no hindrance for the patient and, on the other hand, that an examination angle of more than 270° will be available around the patient's thorax.

Figure 3:
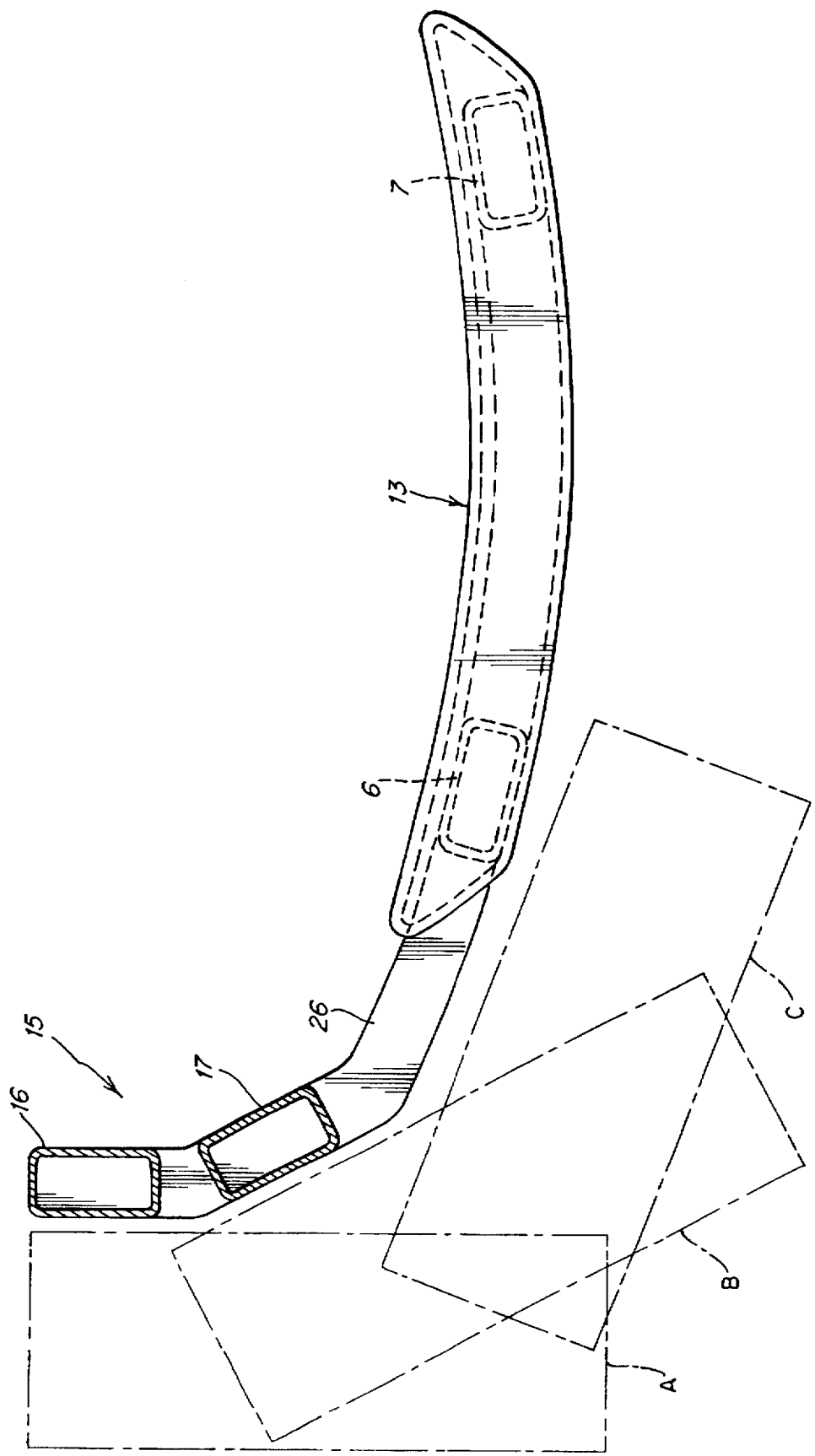
FIG. 3 represents the preferred curvature for the arch shown by a sectional view through plane P of FIG. 2.

In order to obtain more freedom of movement for detectors 2 and 3 of gamma camera 1, arch 15 should be placed as near as possible to the patient. A trade-off imposes a certain curvature for arch 15 in relation to the plane of the bed to skirt round the patient as close as possible. For manufacturing reasons, an approximation of the curvature by multiple angles has been retained, this being represented on the section on FIG. 3. FIG. 3 shows a preferred dual angle with, in dotted lines, positions A, B and C taken by the detector during the possible movements.

As the arch is submitted to high torsional stresses, it preferably consists of two bars 16 and 17, for example of rectangular section, measuring 20×50 mm, which are attached together by one end to a first arm 26 and by the other end to a second arm 27, by mechanical welding. The first arm 26 is securely attached to first part 13. The second arm 27 is securely attached to second part 14.

Certain persons have the particularity of having their heart on the right whereas most persons have them on the left. This is why the possibility of having a removable arch 15 which can be installed both on the right and the left of the platform is provided to reduce imaging hindrance to a minimum. For this, the two arms 26 and 27 can slide in two slides 36 and 37. The first slide 36 is attached by mechanical welding to first part 13. The second slide 37 is attached by mechanical welding to second part 14. The fits between the two arms 26 and 27 and the two slides 36 and 37 are especially accurate to allow easy installation and retention in a stable position. A safety pin, not shown, holds the arch in position.

Window 12 is more transparent to gamma radiation than the rest of the platform. In one example, there is only air in the radiation trajectory between the patient and the detector. But, for cardiac tomographies, examination times are fairly long. It is advisable to support the patient to avoid fatigue, discomfort and therefore movement. To this end, we place a sheet 20 made of a material very transparent to gamma- and X-radiation, preferably tensioned, in this window. We can, for example, use a sheet of polyester film marketed under the trademark Mylar.

The weight of the patients and the installation-removal of this sheet may cause it to distort. To remedy this, a tensioning system compensates for sheet distortion.

For example, the tensioning system represented on FIG. 4a includes an attaching item 18, attaching first part 13 and a straight L-shaped bar 19. This L-shaped bar 19, perpendicular to the longitudinal direction of patient-carrier bed 5, is used to attach, by overlapping and clamping, sheet 20 on one of its sides to first part 13. The other side of sheet 20 is attached to second part 14, by clamping, using a straight U-shaped bar 21. This U-shaped bar 21 sliding longitudinally to patient-carrier bed 5 on second part 14 includes a hole 28 to accommodate screw 22 which passes through second part 14. The end of screw 22 which protrudes from second part 14 is screwed into a wheel 23 to tighten and tension sheet 20.

It is also possible to replace this tensioning system by a movable frame system 30, represented on FIG. 4b, that a man of the trade could define himself in a material as transparent to gamma radiation as the sheet which covers the window. This removable frame 30 consists of a rectangular frame with dimensions same as the window and bears on the platform on each side of the window. A sheet 20 is attached to the upper face of the frame by means of suitable fasteners. The use of such a frame makes utilisation easier as it can be held simply by gravity or be installed on slides between first part 13 and second part 14. A frame tensioning system can also be considered for the above mentioned reasons.

Figure 5:
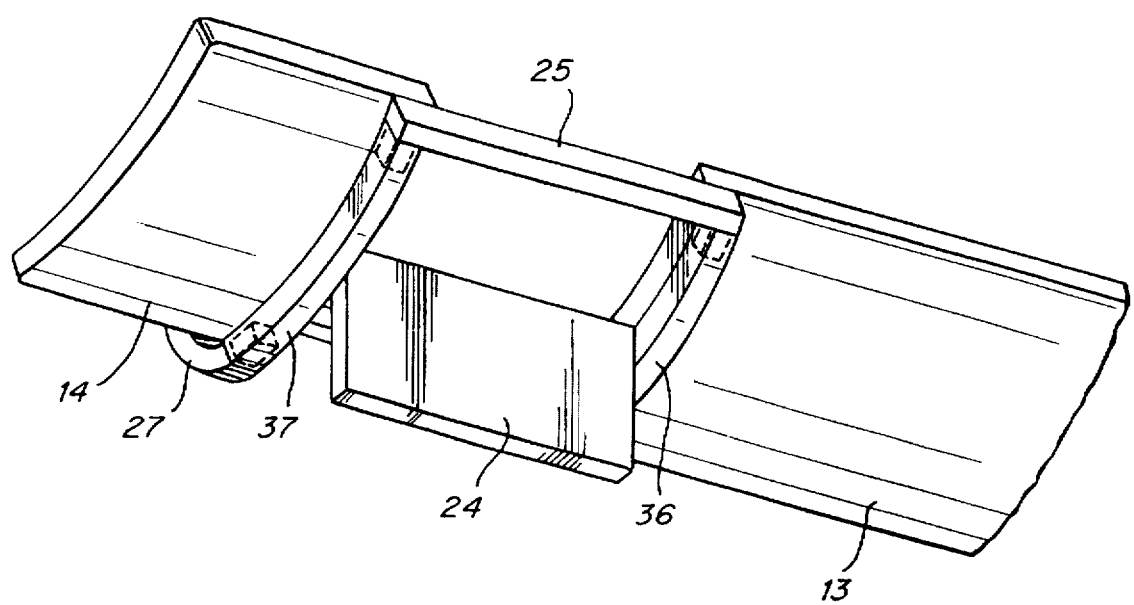
FIG. 5 represents the details of an attenuator separator shown by a three-quarter rear view.

If one wishes to conduct a mammography with the breasts hanging, the image of one breast may show interference caused by the other breast. To improve the possibilities of the system, a separator 24, represented on FIG. 5, can be added perpendicularly to the platform plane. This mammary image separator 24 isolates the radiation of each of the breasts. This separator 24 is attached between first part 13 and second part 14 using the same attaching means as that of sheet 20. For the sheet 20 tensioning system, we will use the tensioner to hold separator 24 in position. For attachment of sheet 20 by removable frame 30, another frame must be provided to carry this separator 24 that will be used for mammographies. This other frame can be made from any material provided that it has a hole on each side of separator 24 allowing the patient's breasts to pass. This separator 24 consists of a plate of a material very opaque to gamma rays; lead, tungsten or gold are suitable. This separator 24 must not protrude beyond the upper part of platform 11 in order not to injure the patient's body. For hygiene and cleanliness reasons, separator 24 will be padded and even covered by a hypoallergenic material.

When the patient is being installed on the patient-carrier bed, kinetic distortions may damage arch 15 which is normally designed to support static distortions. This is why a removable reinforcement 25 is placed on the side opposite arch 15 between first part 13 and second part 14 to stiffen platform 11 during the installation of the patient. The attachments of this removable reinforcement 25 are of same type as those of removable arch 15. It uses the same slides 36 and 37 and a safety position retention safety device by a pin same as that of arch 15. Thus, irrespective of the choice made concerning position of arch 15 in relation to platform 11, removable reinforcement 25 can be used on the edge opposite platform 11. The removable reinforcement 25 is removed to conduct the examinations in order not to disturb the detectors.

Other examinations require patient-carrier beds with other features. The complete patient-carrier bed 5 is relatively costly and large, it is therefore beneficial to be able to conserve the same base and use a removable platform 11. Removability of platform 11 must be ensured in a safe and rapid manner. The inventor has therefore imagined the slide system represented on FIGS. 6, 7, 8, 9.

Figure 6:
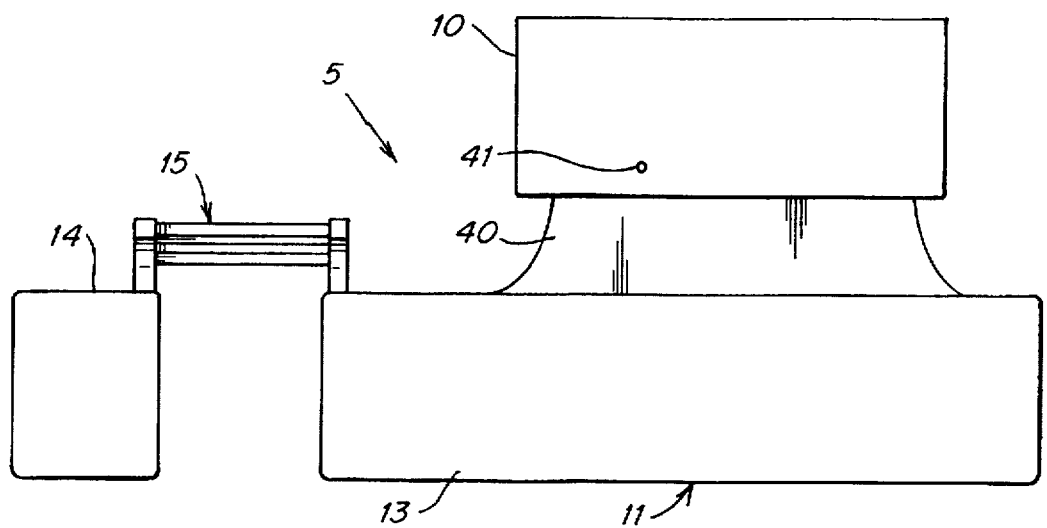
FIG. 6 represents the top view of a patient-carrier bed with a removable platform.
Figure 7:
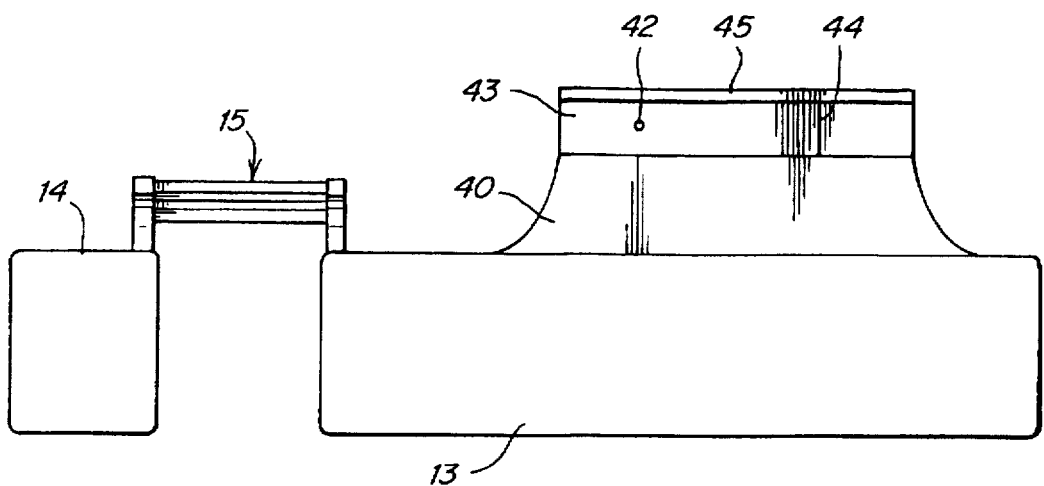
FIG. 7 represents the top view of a removable platform with details of its attaching rail.

FIG. 6 shows a top view of patient-carrier bed 5. We can see platform 11 attached to base 10 by means of an attaching lug 40 and a pin 41. FIG. 7 shows the platform detached from the base. An attaching rail 43 is added to this attaching lug 40. This attaching rail 43 includes a first shoulder 44, located around one quarter of the way along the length of attaching rail 43, a first hole 42, and a tab 45. Tab 45 is located on the side opposite platform 11 and extends upwards. The first shoulder 44 causes on an end of attaching rail 43 a thickness lower than the rest of the attaching rail 43.

Figure 8:
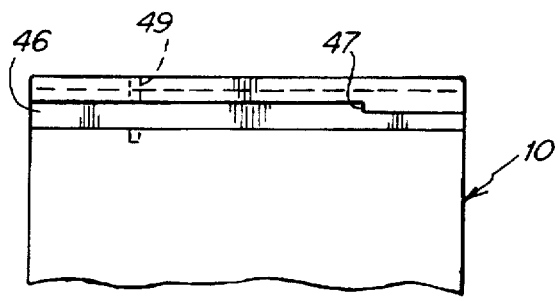
FIG. 8 represents a partial front view of the base of a patient-carrier bed showing details of the attaching slide.
Figure 9:
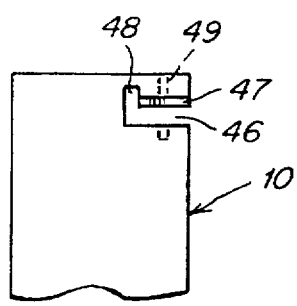
FIG. 9 represents a partial Left Hand view of the base to show the profile of the slide.

Base 10 includes a third slide 46 with a profile reflecting attaching rail 43 as can be seen on FIGS. 8 and 9. This third slide 46 includes a second shoulder 47, a slot 48 at the bottom of the third slide 46, and a second hole 49 which aligns with the first hole 42 when attaching rail 43 is positioned in the third slide 46.

To assemble platform 11 and base 10, we slide attaching rail 43 in the third slide 46. The first shoulder 44 and the second shoulder 47 define a press fit area. When platform 11 is installed, three quarters of attaching rail 43 are easily inserted into the third slide 46, the last quarter requires higher thrust, for example 10 kg of thrust, this ensures retention of platform 11 in position by friction. When shoulders 44 and 47 bear on each other, the platform is in utilisation position. Tab 45 which fits into groove 48 prevents platform 11 from being torn out by the weight of the patient. Pin 41 which fits into the first hole 42 and the second hole 49 is a safety device preventing attaching rail 43 from sliding in the third slide 46 throughout the examination.

We claim:

1. A gamma camera equipped with at least two radiation detectors inclined in relation to each other and a patient-carrier bed including a platform which includes a window more transparent to radiation than the rest of the platform, wherein the platform includes two parts defining the window therebetween and connected to each other by a lateral arch, the arch having a curvature with a change of curvature in relation to a curvature of the platform, the change of curvature occurring at a defined distance from an edge of the platform.

2. The gamma camera according to claim 1, wherein the arch extends beyond a lateral edge of the patient-carrier bed.

3. The gamma camera according to claim 1, wherein the arch has multiple angles in relation to a plane of the patient-carrier bed.

4. The gamma camera according to claim 1, wherein the arch is removable.

5. The gamma camera according to claim 1, wherein the window includes a sheet made of a material more transparent to gamma radiation than the rest of the platform.

6. The gamma camera in according to claim 5, wherein the platform includes a tensioner to tension the sheet in the window.

7. The gamma camera in according to claim 5, wherein the sheet is held on a first removable frame.

8. The gamma camera according to claim 1, wherein the window includes a removable separator made of a metal not transparent to radiation, the separator being positioned in a plane perpendicular to a plane of the platform of the patient-carrier bed.

9. The gamma camera according to claim 8, wherein the patient-carrier bed includes a second removable frame that is adapted to conduct mammographies, the second removable frame having two holes of sufficient dimensions to each let a breast pass therethrough without deforming the breast.

10. The gamma camera according to claim 1, wherein the platform includes a removable reinforcement to be placed on an edge of the window to stiffen the window when installing a patient.

11. The gamma camera according to claim 1, wherein the platform is removable.

12. A gamma camera equipped with at least two radiation detectors inclined in relation to each other and a patient-carrier bed including a platform which includes a window more transparent to radiation than the rest of the platform, wherein the platform includes two parts defining the window therebetween and connected to each other by a lateral arch, the window including a sheet made of a material more transparent to gamma radiation than the rest of the platform, the platform including a tensioner to tension the sheet in the window.

13. A gamma camera equipped with at least two radiation detectors inclined in relation to each other and a patient-carrier bed including a platform which includes a window more transparent to radiation than the rest of the platform, wherein the platform includes two parts defining the window therebetween and connected to each other by a lateral arch, the window including a sheet made of a material more transparent to gamma radiation than the rest of the platform, the sheet being held on a first removable frame.

14. A gamma camera equipped with at least two radiation detectors inclined in relation to each other and a patient-carrier bed including a platform which includes a window more transparent to radiation than the rest of the platform, wherein the platform includes two parts defining the window therebetween and connected to each other by a lateral arch, the window including a removable separator made of a metal not transparent to radiation, the separator being positioned in a plane perpendicular to a plane of the platform of the patient-carrier bed.

15. The gamma camera according to claim 14, wherein the patient-carrier bed includes a second removable frame that is adapted to conduct mammographies, the second removable frame having two holes of sufficient dimensions to each let a breast pass therethrough without deforming the breast.

16. A gamma camera equipped with at least two radiation detectors inclined in relation to each other and a patient-carrier bed including a platform which includes a window more transparent to radiation than the rest of the platform, wherein the platform includes two parts defining the window therebetween and connected to each other by a lateral arch, the platform including a removable reinforcement to be placed on an edge of the window to stiffen the window when installing a patient.

\* \* \* \* \*